(12) United States Patent
Rotilio et al.

(10) Patent No.: US 11,596,480 B2
(45) Date of Patent: Mar. 7, 2023

(54) NAVIGATION, TRACKING AND GUIDING SYSTEM FOR THE POSITIONING OF OPERATORY INSTRUMENTS WITHIN THE BODY OF A PATIENT

(71) Applicant: R.A.W. S.R.L., Busto Arsizio (IT)

(72) Inventors: Alessandro Rotilio, Busto Arsizio (IT); Marco Solbiati, Busto Arsizio (IT)

(73) Assignee: R.A.W. S.R.L., Busto Arsizio (IT)

( * ) Notice: Subject to any disclaimer, the term of this patent is extended or adjusted under 35 U.S.C. 154(b) by 1033 days.

(21) Appl. No.: 16/220,809

(22) Filed: Dec. 14, 2018

(65) Prior Publication Data

US 2019/0183586 A1 Jun. 20, 2019

Related U.S. Application Data

(63) Continuation of application No. 15/775,772, filed as application No. PCT/IB2016/057001 on Nov. 21, 2016.

(51) Int. Cl.
*A61B 34/20* (2016.01)
*G02B 27/01* (2006.01)
(Continued)

(52) U.S. Cl.
CPC .............. *A61B 34/20* (2016.02); *A61B 90/36* (2016.02); *G02B 27/017* (2013.01);
(Continued)

(58) Field of Classification Search
CPC . A61B 34/20; A61B 90/36; A61B 2034/2046; A61B 2034/2048; A61B 2034/2055; A61B 2034/2057; A61B 2034/2061; A61B 2034/2063; A61B 2090/062; A61B 2090/065;
(Continued)

(56) References Cited

U.S. PATENT DOCUMENTS 5,337,758 A * 8/1994 Moore ................ A61B 5/1126
600/595
5,526,812 A 6/1996 Dumoulin et al.
(Continued)

FOREIGN PATENT DOCUMENTS

| EP | 2737868 A1 | 6/2014 |
|---|---|---|
| WO | 2009/083191 A1 | 7/2009 |
| WO | 2017/089941 A1 | 6/2017 |

OTHER PUBLICATIONS

International Preliminary Report on Patentability (Chapter I) for PCT/IB2016/057001 filed on Nov. 21, 2016 on behalf of RAW. S.r.l, dated May 29, 2018. 8 pages.

(Continued)

*Primary Examiner* — Sean D Mattson
(74) *Attorney, Agent, or Firm* — Steinfl + Bruno LLP

(57) ABSTRACT

A navigation, tracking and guiding system for the positioning of operatory instruments inside the body of a patient. The system includes a control unit, a viewer and detecting means for determining the spatial position of the viewer. The system further includes a sensor associated to an operatory instrument and insertable inside the internal portion of the body of the patient. The control unit is configured to project on the viewer an image of the state of the internal portion.

3 Claims, 4 Drawing Sheets

(51) Int. Cl.
*A61B 90/00* (2016.01)
*A61B 90/50* (2016.01)

(52) U.S. Cl.
CPC .. *G02B 27/0172* (2013.01); *A61B 2034/2046* (2016.02); *A61B 2034/2048* (2016.02); *A61B 2034/2055* (2016.02); *A61B 2034/2057* (2016.02); *A61B 2034/2061* (2016.02); *A61B 2034/2063* (2016.02); *A61B 2090/062* (2016.02); *A61B 2090/065* (2016.02); *A61B 2090/066* (2016.02); *A61B 2090/0807* (2016.02); *A61B 2090/365* (2016.02); *A61B 2090/367* (2016.02); *A61B 2090/3983* (2016.02); *A61B 2090/502* (2016.02); *G02B 2027/014* (2013.01); *G02B 2027/0138* (2013.01); *G02B 2027/0141* (2013.01); *G02B 2027/0178* (2013.01); *G02B 2027/0187* (2013.01)

(58) Field of Classification Search
CPC ...... A61B 2090/066; A61B 2090/0807; A61B 2090/367; A61B 2090/3983; A61B 2090/502; A61B 2090/365; G02B 27/017; G02B 27/0172; G02B 2027/0138; G02B 2027/014; G02B 2027/0141; G02B 2027/0178; G02B 2027/0187
See application file for complete search history.

(56) References Cited

U.S. PATENT DOCUMENTS

| | | | |
|---|---|---|---|
| 5,577,502 A * | 11/1996 | Darrow | A61B 34/20 600/534 |
| 6,033,415 A | 3/2000 | Mittelstadt et al. | |
| 6,847,336 B1 | 1/2005 | Lemelson et al. | |
| 7,493,153 B2 | 2/2009 | Ahmed et al. | |
| 7,501,995 B2 | 3/2009 | Morita et al. | |
| 7,774,044 B2 | 8/2010 | Sauer et al. | |
| 9,538,962 B1 * | 1/2017 | Hannaford | A61B 5/7445 |
| 2002/0082498 A1 | 6/2002 | Wendt et al. | |
| 2004/0047044 A1 | 3/2004 | Dalton | |
| 2004/0078036 A1 | 4/2004 | Keidar | |
| 2005/0020910 A1 | 1/2005 | Quadling et al. | |
| 2005/0180470 A1 * | 8/2005 | Sadot | G01J 9/0246 372/20 |
| 2005/0203380 A1 * | 9/2005 | Sauer | A61B 34/20 600/417 |
| 2006/0089626 A1 | 4/2006 | Vlegele et al. | |
| 2007/0273610 A1 | 11/2007 | Baillot | |
| 2008/0194973 A1 * | 8/2008 | Imam | A61B 90/39 600/478 |
| 2011/0046483 A1 | 2/2011 | Fuchs et al. | |
| 2011/0069159 A1 | 3/2011 | Soler et al. | |
| 2013/0267838 A1 | 10/2013 | Fronk et al. | |
| 2014/0022283 A1 | 1/2014 | Chan et al. | |
| 2014/0121660 A1 | 5/2014 | Hauck | |
| 2016/0324580 A1 * | 11/2016 | Esterberg | G06F 3/011 |
| 2016/0364878 A1 | 12/2016 | Guo et al. | |
| 2017/0178375 A1 | 6/2017 | Benishti et al. | |
| 2017/0367771 A1 * | 12/2017 | Tako | A61B 34/20 |
| 2018/0344408 A1 * | 12/2018 | Rotilio | A61B 34/20 |

OTHER PUBLICATIONS

International Search Report for PCT/IB2016/057001 filed on Nov. 21, 2016 on behalf of R.A.W. S.r.l, dated Feb. 20, 2017. 6 pages.
Written Opinion for PCT/IB2016/057001 filed on Nov. 21, 2016 on behalf of R.A.W. S.r.l, dated Feb. 20, 2017. 7 pages.
Non-Final Office Action for U.S. Appl. No. 15/775,772, filed May 11, 2018, on behalf of R.A.W. S.r.L, dated Dec. 8, 2021. 40 pages.

* cited by examiner

NAVIGATION, TRACKING AND GUIDING SYSTEM FOR THE POSITIONING OF OPERATORY INSTRUMENTS WITHIN THE BODY OF A PATIENT

CROSS-REFERENCE TO RELATED APPLICATIONS

The present application is the continuation of U.S. patent application Ser. No. 15/775,772 filed on May 11, 2018 which is the U.S. National Stage of International Patent Application No. PCT/IB2016/057001 filed on Nov. 21, 2016 the contents of each of which are incorporated herein by reference in their entirety.

FIELD

The present invention relates to a navigation, tracking and guiding system for the placement of operatory instruments within the body of a patient in which augmented reality is used as the operator interface.

The system of the present invention is particularly suitable for applications such as diagnostic radiology, oncological surgical radiology, vascular surgical radiology, procedures performed by the insertion of probes and/or needles (such as biopsies and liquid aspirations) and neurosurgery.

BACKGROUND

To date, in the field of surgery and surgical navigation, the use of systems employing radiological images and interfacing them with the ultrasound probe movement is known.

For example, during these types of surgical navigation, systems equipped with computerized tomography (CT) devices are used, which provide radiological images in real time and during the operation (intraoperatory CT scans).

There are also other known systems that can provide the virtual tracking of ablation probes but without giving any information concerning deformation.

On the other hand, the use of operating room eyeglasses provided with a display for viewing images is known. For this purpose, the document EP2737868A1 describes a system that includes a wireless surgical magnifying lens, which allows a user who uses the wireless lens during the execution of a procedure to transmit the information acquired from the wireless lens, and to view patient information on a display. In this way, the transmitted information may be used to assist the procedure in the operating room and improve instructions and to be recorded for later use.

Furthermore, document U.S. Pat. No. 6,847,336 B1 describes a system and a method for the display of data on a translucent screen mounted in the normal field of view of a user. The screen can be mounted on the user's head, or mounted on a mobile structure and positioned in front of the user. A user interface is displayed on the screen, including a movable cursor and a menu of computer control icons. An "eye tracking" system is mounted in the vicinity of the user and is used to control the movement of the cursor.

Additionally, document U.S. Pat. No. 7,501,995B2 describes a system and a method for the presentation of clinical support information which employs eyesight-assisted navigation.

Furthermore, document WO2009083191A1 describes a selective display system which allows to selectively display data and information on a display device mounted on glasses.

On the other hand, the reconstruction of medical images through 3D three-dimensional display is equally known, wherein the three-dimensional tracking of the volume on the patient is provided, as well as, possibly, also the tracking of the needle in the various medical and surgical application fields.

For example, document U.S. Pat. No. 5,526,812A describes a display system which allows to increase and improve the display of body structures during medical procedures.

Other examples of systems and methods of navigation in augmented reality in the medical interventions-related procedures are described in documents U.S. Pat. No. 7,774,044 B2, US 2002/0082498 A1 and US 2013/0267838 A1.

Although all the above-listed systems describe various operator assistance methods during surgery, there are still some limitations in the case of minimally invasive interventions.

In fact, in the case of minimally invasive interventions, the insertion of surgical instruments inside the patient, i.e. probes, able to perform operations without opening the body of a patient, is provided. Such interventions are complicated because of the difficulties in accurately estimating the position of the tissues on which it is necessary to operate and of the instruments to be inserted. For this complexity, errors often occur during surgery completion.

These systems combine the use of ultrasound, characterized by a low spatial resolution, the display of radiological images, characterized by high resolution, through tracking of the ultrasound probe(s) for minimally invasive interventions with electromagnetic sensors or optical systems, without or with low spatial resolution.

SUMMARY

In this context, the technical task underlying the present invention is to propose a navigation, tracking and guiding system/method for the positioning of operatory instruments within the body of the patient that overcomes one or more drawbacks of the prior art mentioned above.

In particular, it is an aim of the present invention to provide a navigation, tracking and guiding system/method and a guide for the positioning of operatory instruments in which augmented reality is used as the operator interface, so as to allow the operator to operate on the patient in a precise, reliable, safe and efficient manner.

Advantageously, the invention relates to a system and a method that brings together different technologies allowing, all together or in combinations thereof, the display, on devices of any type, of images related to internal structures of the body of a patient (of biomedical, physiological and pathological type) and referring to operatory instruments partially inserted within the body of the patient, both therefore not externally visible to the operator, unless the body of the patient is opened. These images, in 2, 3 or 4 dimensions, are made visible to the operator in positions corresponding to the real position in space of the structures that they represent.

Advantageously, according to the invention, the display also concerns the use, tracking and positioning of surgical instruments for a particular focus on the "targeting" of pathologies within the human body.

Therefore, the present invention provides a system and a method of navigation, tracking and guiding for the placement of operatory instruments within a patient in which augmented reality is used as an operator interface to view in real time the internal operation area of the patient in the exact actual external position of a patient.

In accordance with a first aspect of the invention, the mentioned technical task and the specified aims are substantially achieved by a navigation, tracking and guiding system for the positioning of operatory instruments within the patient, comprising the technical features set out in one or more of the appended claims.

In particular, the present invention provides a navigation, tracking and guiding system for the positioning of operatory instruments within the body of a patient, comprising:
- a control unit configured to receive a plurality of information related to the internal state of the body of a patient,
- a viewer configured in such a way that an operator can see at least one internal portion of the body of a patient through the viewer, and
- first detecting means for determining the spatial position of the viewer.

The control unit is configured to project on the viewer an image of the internal state of the internal portion of the body of a patient, wherein the image is obtained by processing the plurality of information on the basis of the spatial position of the viewer.

Advantageously, the system further comprises a probe associated to an operatory instrument and insertable within the portion of the body of a patient, wherein the probe comprises at least one optical guide having dispersion zones of a luminous flux generated inside the optical guide and detecting means of the dispersion of the luminous flux in order to identify the spatial arrangement of the probe when inserted within the patient.

Advantageously, the control unit is also configured to project on the viewer the image of the probe, based on the identified spatial arrangement.

The dependent claims, included herein for reference, correspond to different embodiments of the invention.

In a second aspect of the invention, the technical task mentioned and the aims specified are substantially achieved by a navigation, tracking and guiding method for the positioning of operatory instruments within the patient, comprising the technical features set out in one or more of the appended claims.

According to the invention, the method comprises the steps of:
- providing a viewer configured in such a way that an operator can see at least one internal portion of the body of the patient (P) through said viewer;
- providing first detecting means for determining the spatial position of the viewer;
- providing a control unit to perform the steps of:
- receiving a plurality of information related to the internal state of the body of a patient,
- processing the plurality of information based on the spatial position of the viewer; and
- projecting on the viewer an image of the internal state of the at least one internal portion of the body of the patient based on the performed processing.

Advantageously, the method comprises the steps of:
- providing a probe associated to an operatory instrument and insertable within the portion of the body of a patient, the probe comprising at least one optical guide having dispersion zones of a luminous flux generated inside said optical guide and detecting means of the dispersion of the luminous flux in order to identify the spatial arrangement of the probe when inserted within the body of the patient,
- furthermore, projecting on the viewer the image of the probe based on the identified spatial arrangement, by the control unit.

The dependent claims, included herein for reference, correspond to different embodiments of the invention.

In a third aspect of the invention, the mentioned technical task and the specified aims are substantially achieved by a navigation, tracking and guiding method for the positioning of operatory instruments within the patient, characterized in that it is performed by a computer, according to the description of the appended claims.

In a fourth aspect of the invention, the mentioned technical task and the specified aims are substantially achieved by a computer program characterized in that it performs the steps of the described method, when running on a computer.

BRIEF DESCRIPTION OF THE DRAWINGS

Further features and advantages of the present invention will become more apparent from the indicative, and therefore non-limiting description of a preferred but not exclusive embodiment of a navigation, tracking and guiding system for the positioning of operatory instruments within the body of a patient, as illustrated in the accompanying drawings, wherein.

DETAILED DESCRIPTION

With reference to the attached figures, 1 generally indicates a navigation, tracking and guiding system for the positioning of operatory instruments within the body of a patient, from now on simply indicated as system 1.

Figure 4:
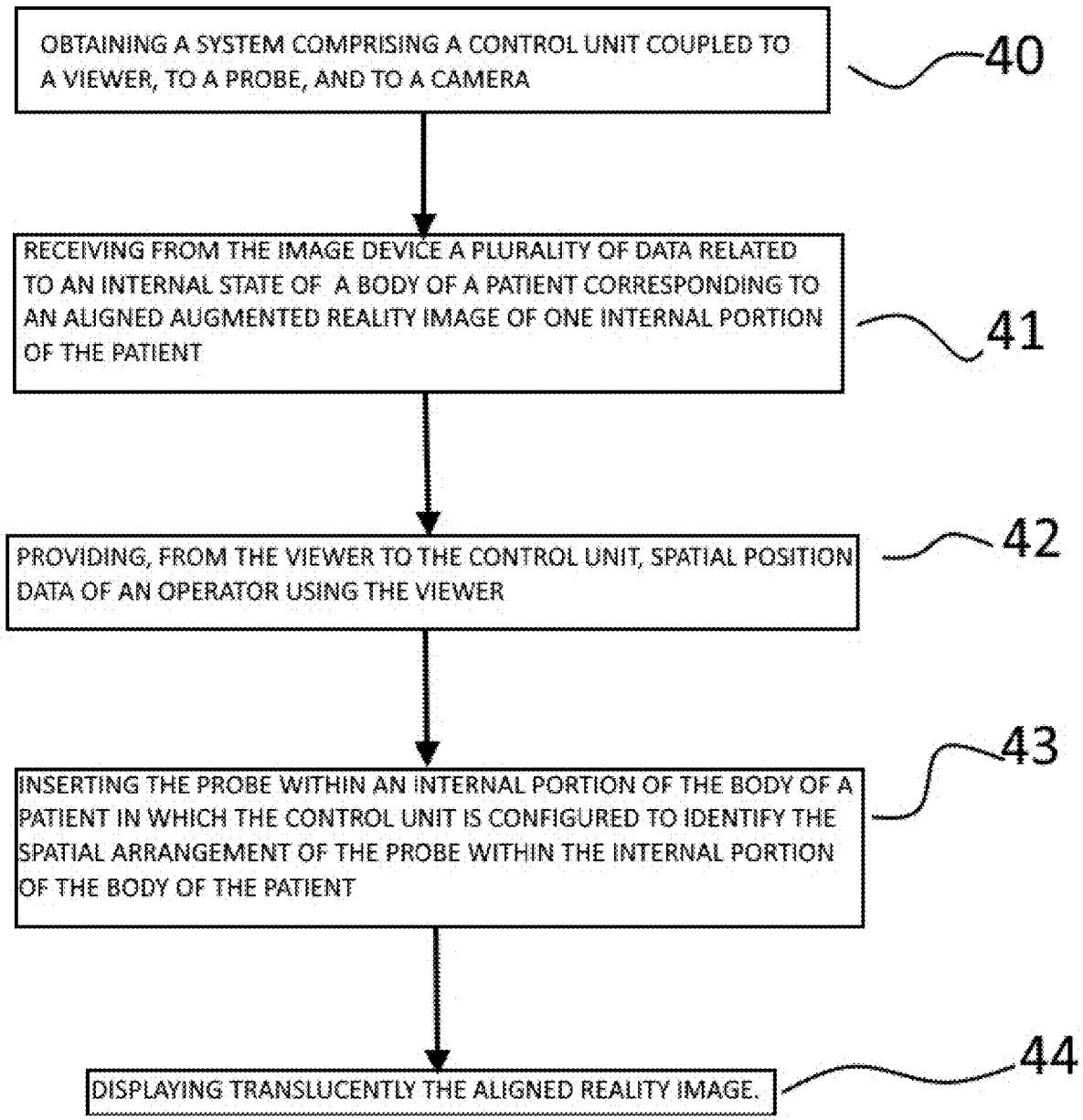
FIG. 4 shows a flow chart for navigation, tracking and guiding system for the positioning of operatory instruments within the body of a patient.

The system 1 comprises a control unit 2 configured to receive a plurality of information related to the internal state of the body of a patient P, see also steps 40 and 41 of FIG. 4.

Preferably, the plurality of information regarding the internal state of the body of a patient P occurs at least through a scan from an image device 4, for example XR (X-ray), MRI (magnetic resonance imaging), CT (computerized axial tomography), PET-CT (computerized positron emission tomography).

The scan can be carried out in situ or be pre-loaded into the control unit 2.

The system 1 comprises a viewer 3 configured in such a way that an operator, not shown, can see at least one internal portion Pi of the body of the patient P through the viewer 3.

The system also comprises the image device 4, also referred to as a first detecting means, for determining the spatial position of the viewer 3.

The control unit 2 is configured to project on the viewer 3 an image of the internal state of the internal portion Pi of the body of a patient P; in particular, the image is obtained by developing the plurality of information on the basis of the spatial position of the viewer 3.

In other words, the control unit 2 can project an augmented reality image of the interior of the body of a patient P on the viewer 3 that varies depending on the spatial arrangement of the viewer 3.

Preferably, the viewer 3 is arranged along an operator—body portion of the patient P visual axis so as to ensure the best ergonomic conditions for the operator and avoid any coordination problems.

Figure 1:
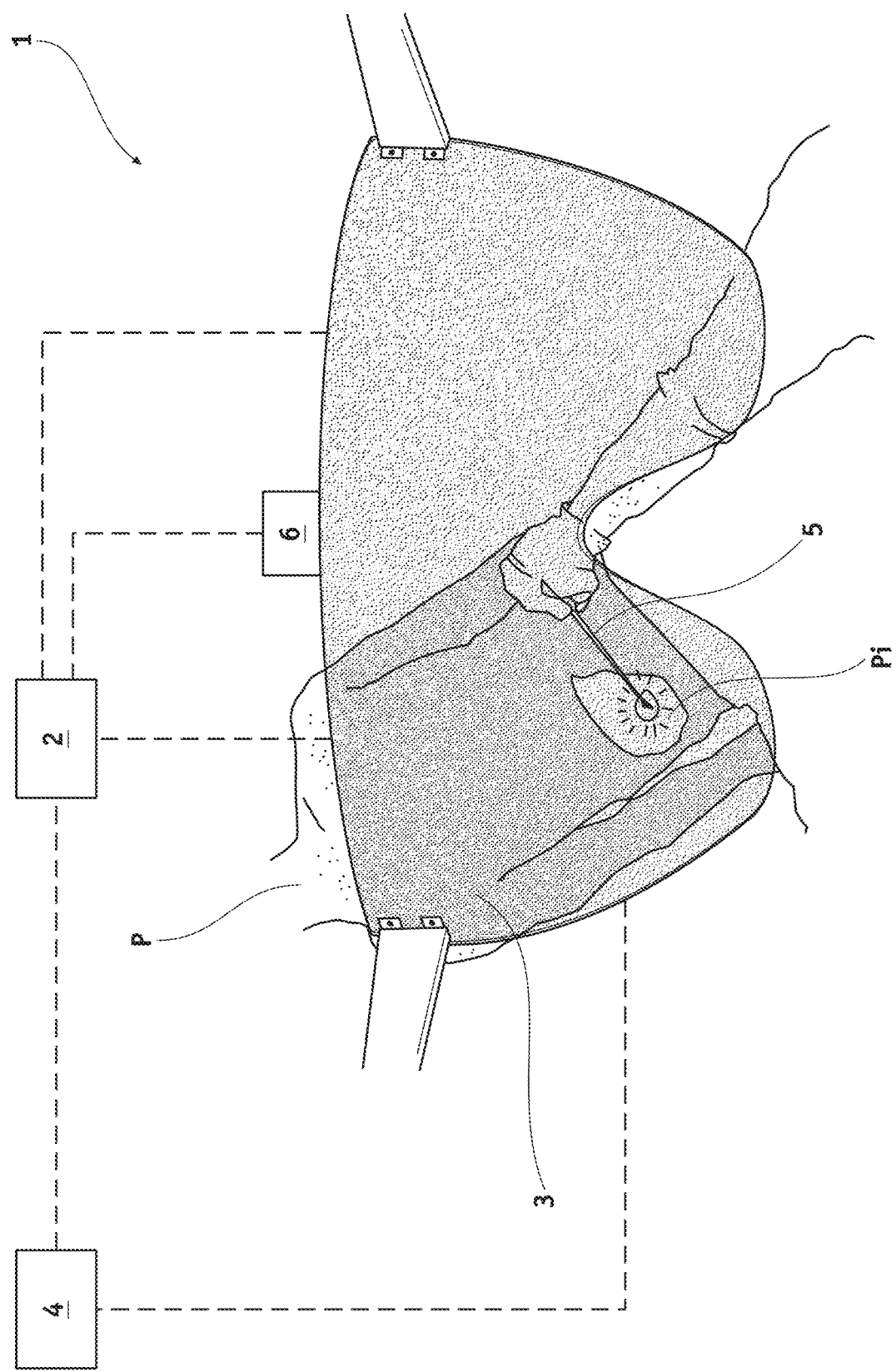
FIG. 1 is a perspective schematic view of a navigation, tracking and guiding system for the positioning of operatory instruments inside the body of a patient according to the present invention during an operating configuration.

Preferably, according to a preferred embodiment of the present invention illustrated in FIG. 1, the viewer 3 is defined by a facial viewer wearable by the operator (also called Head Mounted Display, HMD), for example eyeglasses with at least partially transparent lenses.

Preferably, the viewer 3 comprises a gyroscope, a compass, and an inertial measurement unit; advantageously, these elements allow a correct and precise identification of the spatial position of the viewer 3.

Preferably, the viewer 3 also comprises a depth sensor adapted to record a reconstructed volume of the patient, which advantageously allows the operator to explore organs and pathologies within the body of the patient P while looking at the same patient P.

Advantageously, the system 1 according to the present invention further comprises a probe 5 associated (i.e., inserted internally) to an operatory instrument and insertable within the portion Pi of the body of the patient P.

Figure 3:
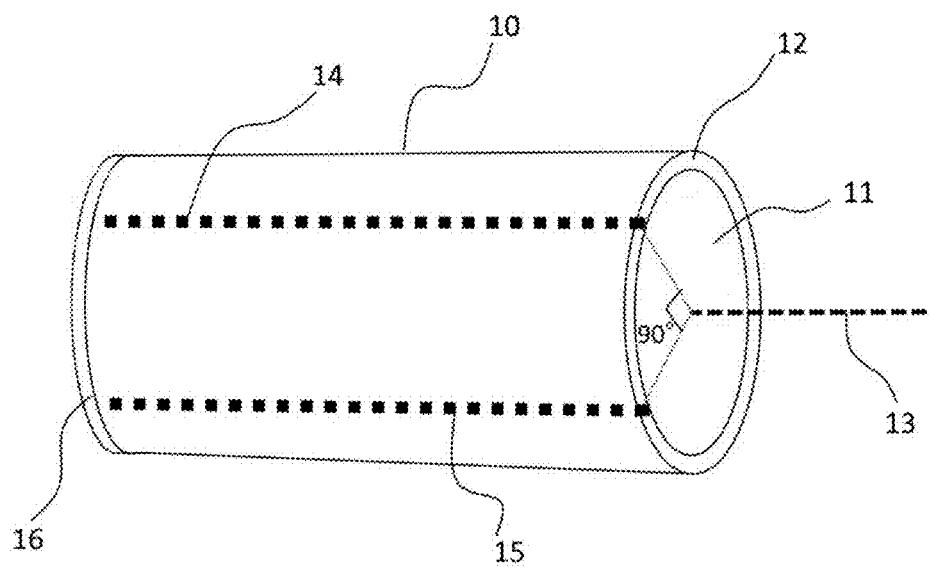
FIG. 3 shows a stylized perspective view of an optical guide.

The probe comprises at least one optical guide as shown in FIG. 3, having first and second dispersion zones 14 and 15 of a luminous flux generated inside the optical guide and detecting means for the detection of the dispersion of the luminous flux, in order to identify the spatial arrangement of the probe 5 when inserted within the patient P.

The control unit 2 is in fact also configured to project on the display of the viewer 3 the image of the probe 5, based on the identified spatial arrangement.

Thanks to the present invention, therefore, the operator can display on the viewer 3 what would not otherwise be visible to the naked eye. In fact, the control unit 2 transmits on the viewer 3 an augmented reality image by showing the internal state portion Pi of the body of the patient P superimposed on an actual image of the body of the same patient P.

The actual image of the patient P visible through the viewer 3 is therefore superimposed on a virtual image projected in transparency, showing the organs and the internal tissues of the patient P together with the probe portion inserted within the patient P that otherwise would not be visible.

Thanks to the present invention, therefore, the operator can operate in absolute safety and precision on the affected area without the need of having to open the body of the patient P to display the operating area and the position/movement of the probe 5 associated with the operatory instruments.

As mentioned above, in order to identify the spatial arrangement of the probe 5 when inserted within the patient P, an optical guide 10 is provided, inside which a luminous flux flows; by modulating and measuring the optical power losses reflected through the first and second dispersion zones 14 and 15, it is possible to determine, and therefore, display on the viewer 3 by means of the control unit 2, the position of the probe 5 within the patient P, see also step 43 in FIG. 4.

Therefore, it is possible to check and display in real time the correct handling of surgical instruments 5 that incorporate probes of the type object of the present invention in order to operate accurately and reliably.

In other words, the optical guide 10 is micro-machined along its central axis 13 in order to introduce reflected optical power losses varying according to the entity and direction of the curvature to which it is subjected.

The first and second dispersion zones (14 and 15) are preferably realized by micro-machining the optical guide 10, which consists of the direct mechanical abrasion of the outer casing of the guide (also called "cladding 12") in order to locally reduce the degree of light confinement in the core 11.

The part of the optical guide 10 subjected to the selective removal of the cladding 12 allows light, no longer confined within the core 11, to escape towards the outside, resulting in a loss of reflected power.

The optical power loss increases or decreases following the positive or negative curvature of the optical guide 10, thus power loss appears to be directly proportional to the curvature of the sensitive area (also called "core 11") of the optical guide 10.

So, according to the principle of operation of the present system 1, the integration of measurement of the probe 5 bending is provided, with position data originating from the image device 4, also referred to as a first detecting means, for determining the spatial position of the viewer 3, see also step 42 in FIG. 4.

According to a possible embodiment of the present invention, the spatial reference system is realized with an articulated arm with five degrees of freedom, which allows to provide Cartesian coordinates X, Y, Z of the probe, with respect to the "operatory field" reference system.

Preferably, the first dispersion zone 14 is arranged in sequence along at least one portion of said optical guide as shown in FIG. 3.

Preferably, the second dispersion zone 15 is arranged in sequence along at least one portion of said optical guide and arranged radially staggered with respect to a central axis 13 of the optical guide as shown in FIG. 3.

Thanks to the staggered configuration of the first and second dispersion zones 14 and 15, it is possible to obtain a precise estimate of the spatial arrangement of the probe 5.

Even more preferably, the second dispersion zone 15 is arranged at a 90° angle with respect to the first dispersion zone 14 in which the angle is measured with respect to a central axis 13 of the optical guide 10 as shown in FIG. 3.

Preferably, the probe 5 comprises a first dispersion zone 14 and a second dispersion zone 15 parallel to each other, in which the first dispersion zone 14 and the second dispersion zone 15 are defined respectively on the optical guide 10 as shown in FIG. 3.

Preferably, the optical guide 10 is connected to a light source, in particular a laser source, not shown, and has a reflecting wall 16 arranged at a free terminal end, wherein between the laser source and the reflective wall a directional coupler is arranged, connected to an oscilloscope.

Advantageously, closing with reflective material the free end of the optical fibre, it is possible to generate a return of the light in the opposite sense.

Preferably, the system comprises a video conversion assembly, not shown, connected to the control unit 2.

Preferably, the video conversion assembly comprises: at least two VGA-HDMI converters, at least one BNC-HDMI converter, and at least two HDMI ports. Still more preferably, the converters are arranged in a single container and the five video signals define the input of a "switcher" and "scaler" with five inputs and a single HDMI output. Video signals are picked up by a switcher and sent in HDMI standard to the viewer 3.

The video signals are sent to the viewer 3 by a mirroring device or by measuring encoder 7; alternatively, it is possible to use a local server.

According to a possible embodiment of the present system, it is expected that the video signals can be selected by the operator by means of a pressure device, for example a pedal.

The pedal is useful for ergonomics during surgery in which the doctor/operator must look different monitors, both during the operation and during the diagnosis, as well as during the targeting in the field of biopsy.

Preferably, the system 1 comprises a camera 6, also referred to as a second detecting means, of the outer surface of the body of the patient P, connected with the control unit 2, for example a stereoscopic camera 6, preferably integral with the viewer 3.

Advantageously, the camera 6, also referred to as a second detecting means, of the outer surface of the body of the patient P allow to record the operation while the operator performs it; also, if installed on the viewer 3, they are especially useful as regards both instructions, because it is possible to obtain directly the clinical point of view, and legal aspects, because they record the entire operation.

Preferably, the viewer 3 comprises a data transmission and reception unit, not illustrated, preferably via Wi-Fi, connected with the first detecting means for determining the spatial position of the viewer 3 and/or connected with the second detecting means 6 of the outer surface of the body of the patient P.

To allow the display of an augmented reality picture as faithful and consistent as possible with the actual internal state of the patient P, it is necessary to take into account the vital parameters of the patient P (breathing, heartbeat, etc.). In fact, the radiological scans can only provide a static image of the interior of the patient P.

For this purpose, it is necessary to identify the variation of the spatial configuration of the outer surface of the body of the patient P that the operator looks through the viewer 3 in order to obtain a correct overlap/projection of the image processed by the control unit 2 on the actual image of the patient P.

The invention provides to arrange seconds detecting means 6 of the outer surface of the body of the patient P connected with the control unit 2.

In particular, the invention provides for arranging at least three first physical markers suitable to be arranged on the outer surface of the body portion Pi of the patient P and detectable by the second detecting means 6 themselves; detecting the dynamic positioning of the first physical markers to send a plurality of information to the control unit 2; and by the control unit 2, aligning the first virtual markers of the image of the internal state projected on the viewer 3 with the first physical markers arranged on the body of the patient P.

In other words, the second detecting means 6 of the outer surface of the body of the patient P comprise at least three first physical markers (preferably electromagnetic or optical), not illustrated in the attached figures, suitable to be arranged on the outer surface of the body portion Pi of the patient P and detectable by the second detecting means 6 themselves. The second detecting means 6 of the outer surface of the body of the patient P detect the dynamic positioning of the first physical markers to send a plurality of information to the control unit 2, which is advantageously configured to align the first virtual markers of the image of the internal state projected on the viewer 3 with the first physical markers arranged on the body of the patient P.

This makes it possible to generate a precise and good-quality augmented reality image that instantly reflects the actual state of the patient inside, the still images having been "corrected" with the vital parameters of the patient P.

The invention provides for arranging a second physical marker disposed on the probe and suitable to be disposed in use outside of the body of the patient P, and also to detect the physical position of the second marker using the second detecting means 6 of the outer surface of the body of the patient P.

In other words, the system 1 comprises a second physical marker disposed on the probe and suitable to be placed in use outside of the body of the patient P, in which the second detecting means 6 of the outer surface of the body of the patient P are configured to also detect the physical position of the second marker.

Advantageously, in this way, it is possible to accurately identify the positioning of the probe 5 inside the body of the patient P and view it in the augmented reality projected on the viewer 3.

It is useful to point out here that the spatial reference may be provided by the fact of anthropomorphic arm employed by the operator, then, in this configuration, the second physical mark can represent an additional piece of information (substantially redundant) but useful to increase the reliability of the system on the position of the probe handle.

Preferably the second detecting means, 6 of the outer surface of the body of a patient comprise at least one of an ultrasound transducer, an inertial measurement unit and a measuring encoder 7, so as to determine in real time said patient's vital parameters.

Figure 2:
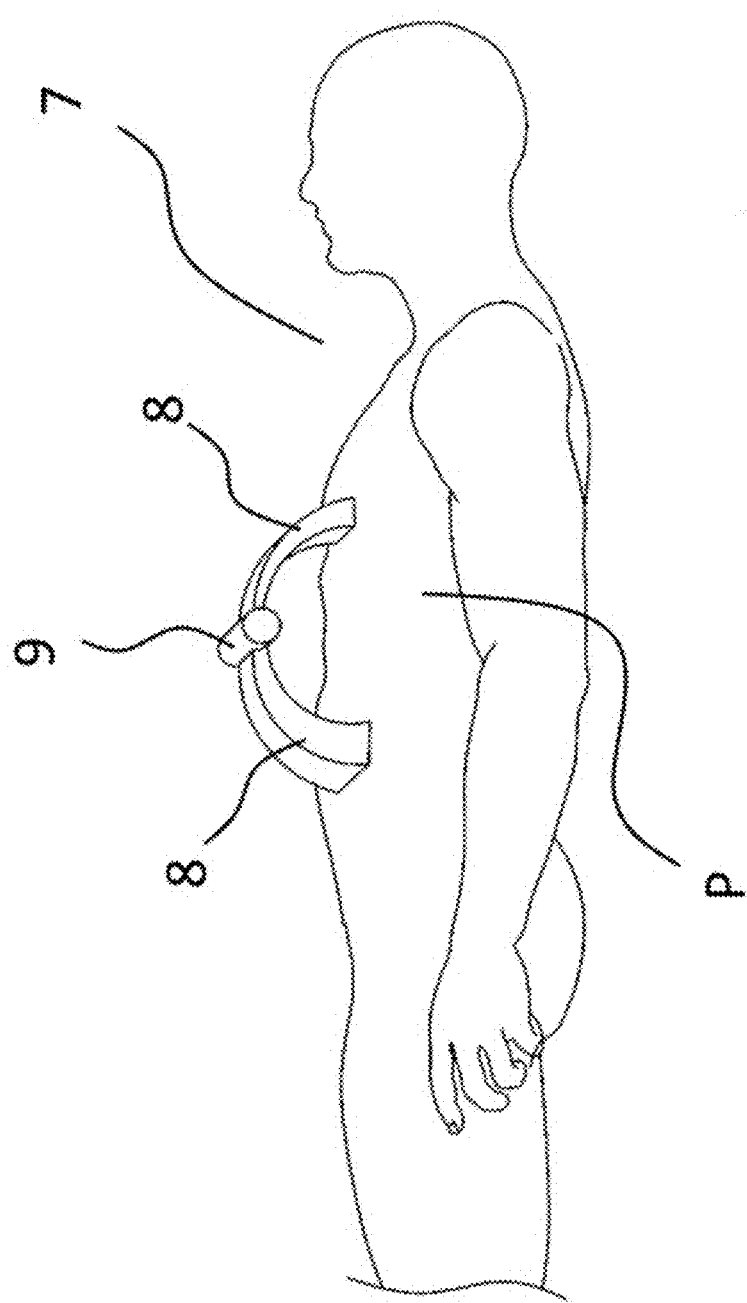
FIG. 2 shows a measuring encoder, i.e. a system composed of at least two arms joined by a joint whose motion is detected by an encoder.

In particular, the measuring encoder 7 is a system composed of at least two arms 8 joined by a joint 9 whose motion is detected by an encoder, as shown in FIG. 2.

The ends of the two arms 8 are fixed to the patient's chest and consequently move according to the patient's chest breathing motion. In so doing, they reveal a dynamic pattern of the respiratory cycle. Every moment of the pattern will be matched with the target position detected at that moment, so as to match each phase of the respiratory cycle, determined in this manner, with a position of the nodule.

Preferably, the system 1 comprises a compactness sensor of the internal tissues of the patient P, preferably a loss-modulation optical fibre interferometric sensor.

Advantageously, thanks to the compactness of the sensor, it is possible to integrate in the plurality of information detected also a measure of the so-called "stiffness", which allows to supply characterization parameters of tissues crossed by the probe.

The present system 1 can be advantageously used during, before, or after surgery. In fact, the system 1 makes it possible for the operator to show an overlap of internal organs and pathologies in 3D, aligned with the real anatomical structures.

Moreover, the present system 1 makes it possible to display operatory instruments inside the body of the patient P and represent their deformation through different anatomical structures, see also step 44 in FIG. 4.

It can be used both for minimally invasive procedures and for standard surgical interventions. The only difference is that, in minimally invasive procedures, all the reconstructed volume of the interior of the body of the patient P is aligned with the body of the patient P; while in the second case, the alignment is made between a specific part of an organ and the same part of the organ in the reconstructed volume. For example, FIG. 1 shows schematically a real segment of the liver and the reconstructed volume of the same.

The system of this invention has many advantages.

The invented solution allows to view subjectively with respect to the operator the images in 2, 3 or 4 dimensions in the exact location where the structure they are referred to are located, with high spatial resolution, and to increase the resolution, accuracy and recognition the correct positioning of the probe 5 associated with the operatory instruments.

In addition, the invented solution allows to detect the position and the bending of the probes and of the deformable instruments.

The system, unlike the solutions used to solve the same problems, allows greater precision, even without electromagnetic systems, through mechanical systems and/or computer vision, together or separately.

The system of the present invention can be used for the preparation or the performance of surgical, laparotomy, endoscopy or minimally invasive interventions, percutaneous or transosseous, or during interventions by laparotomy or endoscopy. The system is also valid for performing percutaneous or radiologically-guided diagnostic procedures, such as, by way of example, biopsy or needle aspiration.

Advantageously, the invention provides that the step of processing the plurality of information on the basis of the spatial position of the viewer 3 comprises processing through segmentation of organs and diseases;

Preferably, the step of processing includes making 3D renderings of radiological scans.

The invention also involves the creation of a 3D representation with the pathology segmented and separated from the rest of the volume as a function of the performed segmentations.

The invention further comprises a step of projecting on the viewer 3 an image of the internal state of the at least one internal portion Pi of the body of the patient P as a function of the performed processing, realized by projecting a joint visualization of organs and pathologies.

As an alternative, advantageously, the invention provides that the step of processing the plurality of information on the basis of the spatial position of the viewer 3 comprises processing via segmentation of organs and post-treatment necrosis;

The invention also involves the creation of a 3D representation with the pathology segmented and separated from the rest of the volume as a function of the performed segmentations.

Preferably, the step of processing includes making 3D renderings of radiological scans.

The invention further comprises a step of projecting on the viewer 3 an image of the internal state of the at least one internal portion Pi of the body of the patient P as a function of the performed processing, realized by projecting a joint visualization of the pathology and necrosis.

In other words, in a first of the two alternatives, the invention provides the use of a computer program capable of producing segmentations of organs and pathologies (such as, for example, tumours, etc.) and a 3D rendering of radiological scans. Moreover, the software is also able to compare 3D renderings from different scans. It consists of software codes that include segmentation algorithms.

The program is, in particular, a web application that can take images from different radiological scans (MRI, CT, PET-CT) and transform them into a 3D representation with the pathology segmented and separated from the rest of the volume (for example, with a different colour). Segmentation is fully automatic, that is without user intervention, and does not need any correction.

In addition, in the second of the two alternatives, the program also measures if the treatment was successful or not. In fact, using this software, organs and post-treatment necrosis are segmented in the images (CT-PET, MRI and CT scans), and the volume is recorded before the treatment and after the treatment, and a joint display of the pathology and the necrosis is performed.

The program expects to receive an image processing request of an internal portion Pi of the body of the patient P and to transmit data representative of the request to the control unit 2.

In other words, a web client requests the execution of a script, the script is placed into a scheduler that will manage the queue/the order of the script to be run on the server and, once the scheduler will give the go-ahead, the server will process the files with the required script and write the files in the shared storage.

The program expects to receive the image of a probe as previously defined and to display the image.

In other words, the web client will find the generated files or the requested layers and will view them on the viewer 3, particularly on the HMD.

Another embodiment of the invention involves the registration of a reconstructed volume of a patient using a depth sensor. This sensor advantageously allows the operator to explore organs and pathologies within the body of the patient P while watching the same patient P.

This is the solution of a second computer program, based on appropriate means adapted to implement the so-called "computer vision".

This second solution involves the use of depth sensors and of a stereoscopic camera, jointly or separately, in such a way that the two volumes are aligned. Said camera is used both in AR recognition and for the generation of a "disparity map" which allows to have more information regarding the depth of the scene; for this second reason, the camera must also have the possibility to adjust the interocular distance of the same, in this case in order to operate with different depth ranges (for example a setting to two/three fixed presets, for a long range and a more accurate short range).

It should be hereby specified that said depth sensor alone would be sufficient to define the depth map of the scene, making it unnecessary to compute a disparity map using a stereoscopic camera, but given that this type of sensors is often susceptible to strong light and infrared ray sources which can interfere with the reading, it is possible and, in some cases, necessary to integrate both technologies to obtain a more precise alignment between reality and augmented reality.

A navigation, tracking and guiding system/method for the positioning of operatory instruments within the body of a patient in which augmented reality is used as an operator interface, so as to allow the operator to operate on the patient in a precise, reliable, safe and efficient manner, has been described.

The invention claimed is:

1. A navigation, tracking and guiding system for positioning operatory instruments within a body of a patient, the system comprising:
   a control unit configured to be coupled to an image device, wherein the control unit is configured to receive a plurality of information data from the image device related to an internal state of the body of the patient corresponding to an aligned augmented reality image of at least one internal portion of the body of the patient;
   a viewer connected to the control unit, the viewer configured to provide spatial position data of an operator wearing the viewer, wherein the viewer is configured to translucently display the aligned augmented reality image;

a probe coupled to the control unit, wherein
the probe is associated to an operatory instrument and insertable within the at least one internal portion of the body of the patient, the probe comprising
(i) at least one optical guide having a central axis, a cladding around a fiber core, and
(ii) first and second dispersion zones micro-machined into the cladding along the central axis, wherein the first and second dispersion zones are parallel to each other and separated from each other by a 90° angle with respect to the central axis of the at least one optical guide
and wherein
a luminous flux generated inside the at least one optical guide is configured to identify a spatial arrangement of the probe when inserted within the body of the patient;

a camera connected to the control unit for photographing a real image of an outer surface of the body of the patient on the viewer; and a measuring encoder comprising two arms joined by a joint in which end portions of the two arms are configured to be fixed to the patient's chest and consequently move according to the patient's chest breathing motion.

2. The system according to claim 1, wherein the aligned augmented reality image of the at least one internal portion of the body of the patient is translucently displayed over the real image of the outer surface of the body of the patient on the viewer.

3. The system according to claim 1, wherein the viewer is a head-mounted augmented reality display.

\* \* \* \* \*